(12) United States Patent
Sato et al.

(10) Patent No.: US 7,774,175 B2
(45) Date of Patent: Aug. 10, 2010

(54) METHOD, APPARATUS, AND COMPUTER-READABLE RECORDING MEDIUM FOR DISPLAYING GENETIC INFORMATION

(75) Inventors: Tomoaki Sato, Kawasaki (JP); Mutsuyo Yamaguchi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 427 days.

(21) Appl. No.: 11/288,167

(22) Filed: Nov. 29, 2005

(65) Prior Publication Data
US 2007/0021928 A1    Jan. 25, 2007

(30) Foreign Application Priority Data
Jul. 21, 2005  (JP)  ............................. 2005-211961

(51) Int. Cl.
*G06F 17/10* (2006.01)
(52) U.S. Cl. ................................ 703/2; 702/19; 703/11; 345/586; 345/589; 345/619; 211/41.12
(58) Field of Classification Search ....................... None
See application file for complete search history.

(56) References Cited
U.S. PATENT DOCUMENTS
2002/0049543 A1 *  4/2002  Nakashige et al. ............ 702/19

2004/0047499 A1 *  3/2004  Shams ......................... 382/129
2005/0037363 A1 *  2/2005  Minor ........................... 435/6

FOREIGN PATENT DOCUMENTS
JP     11-342000     12/1999

OTHER PUBLICATIONS
"KEGG Pathway Database", <URL: http://www.genome.jp/kegg/pathway.html>, 2005, 5 pages.
"BioCarta—Charting Pathways of Life", <URL: http://www.biocarta.com>, 2005, 1 page.

* cited by examiner

*Primary Examiner*—Carolyn L. Smith
(74) *Attorney, Agent, or Firm*—Staas & Halsey LLP

(57) ABSTRACT

Pie charts are respectively displayed at coordinate locations in each upper left corner of image data that indicates genes on a network diagram N by a genetic information display apparatus. These pie charts can also be displayed semi-transparently. Numerical values of gene expression information (including a first expression level, its expression level ratio, a second expression level and its expression level ratio) prior to a scale conversion can also be displayed by pointing to image data using a pointing device. Accordingly, the legibility of the gene expression information is enhanced, and can be understood intuitively and clearly.

7 Claims, 9 Drawing Sheets

FIG.3

| GENE | X COORDINATE | Y COORDINATE |
|---|---|---|
| G1 | x1 | y1 |
| G2 | x2 | y2 |
| ⋮ | ⋮ | ⋮ |
| Gi | xi | yi |
| ⋮ | ⋮ | ⋮ |
| Gn | xn | yn |

FIG.6

| GENE | EXPRESSION LEVEL S1i OF GROUP I | EXPRESSION LEVEL S2i OF GROUP II | PIE CHART ANGLE T1i OF GROUP I | PIE CHART ANGLE T2i OF GROUP II | PIE CHART RADIUS D1i OF GROUP I | PIE CHART RADIUS D2i OF GROUP II |
|---|---|---|---|---|---|---|
| G1 | 528.05 | 221.76 | 0.5 | -0.37 | 46 | 39 |
| G2 | 60.0677 | 421.9333 | -0.7959 | 0.434 | 30 | 44 |
| ... | ... | ... | ... | ... | ... | ... |
| Gi | 1757.342 | 311.3996 | 0.9627 | -0.6522 | 55 | 42 |
| ... | ... | ... | ... | ... | ... | ... |
| Gn | 76.8 | 51.3 | 0.9027 | 0.4397 | 31 | 29 |

METHOD, APPARATUS, AND COMPUTER-READABLE RECORDING MEDIUM FOR DISPLAYING GENETIC INFORMATION

CROSS-REFERENCE TO RELATED APPLICATIONS

This application is based upon and claims the benefit of priority from Japanese Patent Application No. 2005-211961, filed on Jul. 21, 2005, the entire contents of which are incorporated herein by reference.

BACKGROUND OF THE INVENTION

1. Field of the Invention

The present invention relates to a technology for displaying genetic information of biological tissues.

2. Description of the Related Art

Determination of the characteristi of the manner and at what time a gene is expressed in a specific tissue is important in terms of understanding the involvement of genes in biophenomena. In particular, a comparison of the transcription levels of two genes between "diseased tissue and normal tissue" and "diseased tissue and drug-administered tissue" is typically carried out, and is frequently used in the clinical and drug development settings.

Since the level of gene expression used as a reference in such comparisons varies considerably depending on the tissue and time, it cannot be determined precisely. Consequently, a characteristic gene is currently specified using the ratio of expression levels between two genes. For example, in the microarray method, which is frequently used to compare gene transcription levels, transcription levels are quantified by labeling mRNA (DNA transcription product) in the body with a fluorochrome dye, causing the dye to emit light, and then detecting the fluorescence intensity (arbitrary units) with a detector.

A system that handles genetic information has been disclosed in, for example, Japanese Patent Application Laid-open No. H11-342000. In this system, the expression levels of predetermined genes collected from two tissue samples are respectively defined as the horizontal or vertical axis, and the expression levels of the predetermined genes are visualized by a computer-assisted comparison of expression arranged at a site selected on the horizontal and vertical axes based on the expressed state in the two tissue samples.

Accompanying increasing activity in research on the interaction between genes and proteins, gene network diagrams are being disclosed on websites and researchers are using those diagrams. Analysis of expression using microarrays and gene chips will be an important key when verifying the interactions between genes in existing network diagrams and attempting to expand upon those diagrams (for example, see "Kyoto Encyclopedia of Genes and Genomes (KEGG)", available online on 13 Jul. 2005, and "BioCarta" available online, on 13 Jul. 2005).

As indicated in Japanese Patent Application Laid-open No. H11-342000, although techniques have been proposed for scoring levels of gene expression by combining the expression levels (intensities) and expression level ratios of genes when administering a drug and not administering a drug for normal tissue and diseased tissue, respectively, since the score is not considered to be intuitive by researchers, it has a problem of being difficult to understand.

When network diagrams disclosed in KEGG and BioCarta are used, the scores for each of the large number of genes in the network diagram must be displayed on a limited screen. Thus, if the scores are comprehensively displayed in the blank areas of the network diagram, in addition to the scores being difficult to understand intuitively, the overall network diagram becomes illegible, resulting in a problem of considerable inconvenience for researchers.

Furthermore, when the expression levels of two genes are compared, for example, even if the expression levels of both genes increased by the same factor of 1.2, when the gene expression level (mRNA level) of a gene A has increased from 2000 to 2400, and the gene expression level (mRNA level) of a gene B has increased from 5 to 6, the increased gene expression levels differ by 400-fold between the gene A and the gene B. In this case, although the phenomenon of increased expression of the gene A is biologically significant, if displayed based on the increase in the gene expression of the gene B, it becomes difficult to observe the biologically significant gene expression of the gene A, thus resulting in a problem of being inconvenient for researchers.

SUMMARY OF THE INVENTION

It is an object of the present invention to at least solve the problems in the conventional technology.

According to an aspect, an apparatus for displaying genetic information includes an acquiring unit configured to acquire, for a gene in the tissue of an organism, a predetermined-conditions-expression level ratio that is a ratio between a reference expression level in a predetermined state of the tissue and a first expression level in a specific state that differs from the predetermined state of the tissue and under predetermined conditions, and an other-conditions-expression level ratio that is a ratio between the reference expression level and a second expression level in the specific state of the tissue and under other conditions that differ from the predetermined conditions; a displaying unit with a display screen; and a display controller configured to control the displaying unit so as to display on the display screen the predetermined-conditions-expression level ratio and the first expression level using a first diagram that includes a graph, and the other-conditions-expression level ratio and the second expression level using a second diagram that includes a graph.

According to another aspect, a method for displaying genetic information includes acquiring, for a gene in the tissue of an organism, a predetermined-conditions-expression level ratio that is a ratio between a reference expression level in a predetermined state of the tissue and a first expression level in a specific state that differs from the predetermined state of the tissue and under predetermined conditions, and an other-conditions-expression level ratio that is a ratio between the reference expression level and a second expression level in the specific state of the tissue and under other conditions that differ from the predetermined conditions; and displaying on a display screen the predetermined-conditions-expression level ratio and the first expression level using a first diagram that includes a graph, and the other-conditions-expression level ratio and the second expression level using a second diagram that includes a graph.

According to still another aspect, a computer-readable recording medium is configured to store therein a computer program that causes a computer to implement a method for displaying genetic information according to the present invention.

The above and other objects, features, advantages and technical and industrial significance of this invention will be better understood by reading the following detailed descrip-

BRIEF DESCRIPTION OF THE DRAWINGS

FIG. 3 is an explanatory diagram of gene coordinate data in a network diagram according to the embodiment;

FIG. 6 is an explanatory diagram of conversion results obtained from a converter according to the embodiment;

DETAILED DESCRIPTION OF THE PREFERRED EMBODIMENTS

Exemplary embodiments of the present invention will be explained below in detail with reference to the accompanying drawings.

Figure 1:
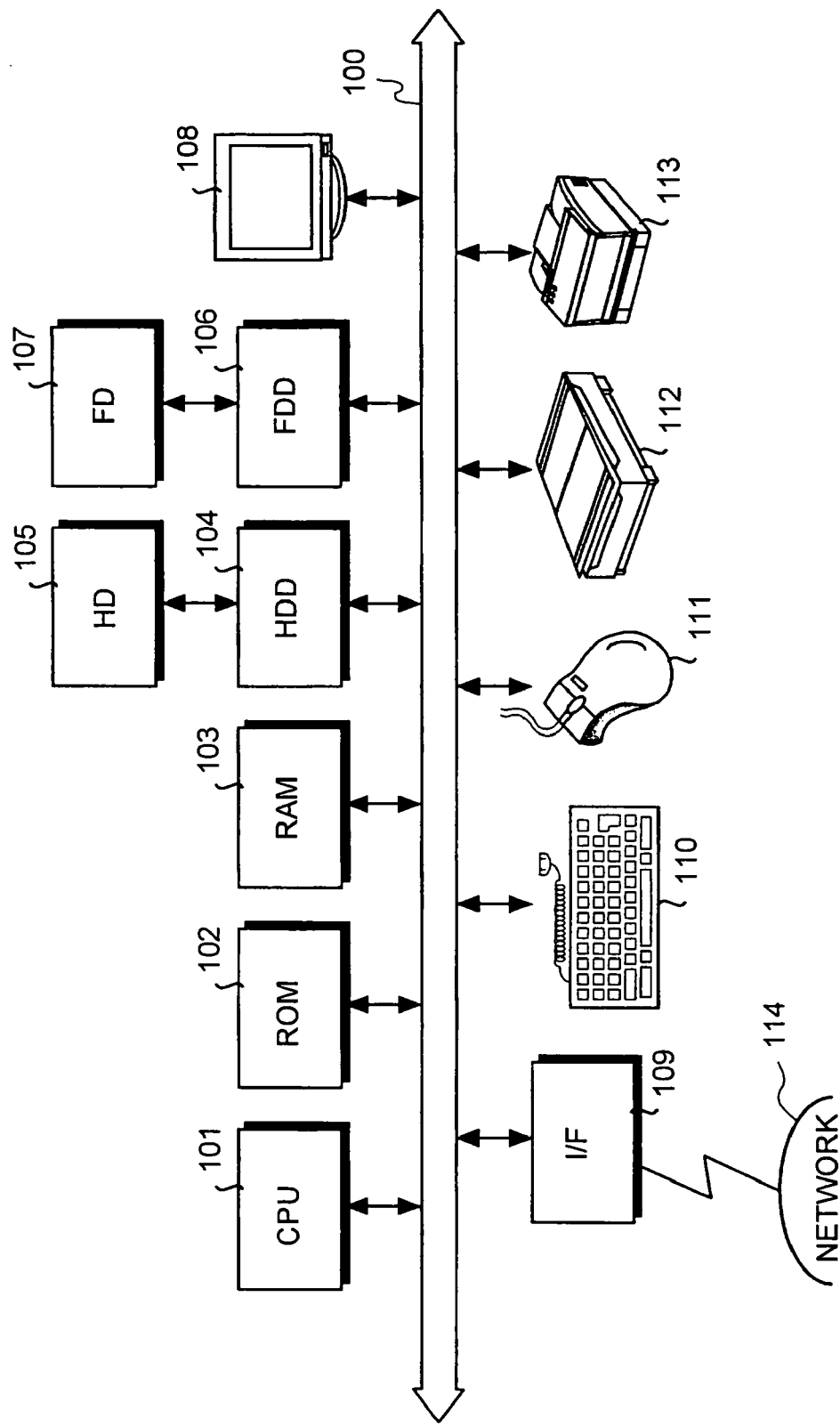
FIG. 1 is a block diagram of the hardware configuration of a genetic information display apparatus according to an embodiment of the present invention.

FIG. 1 is a block diagram of the hardware configuration of a genetic information display apparatus according to an embodiment of the present invention.

In FIG. 1, a genetic information display apparatus includes a central processing unit (CPU) 101, a read only memory (ROM) 102, a random access memory (RAM) 103, a hard disk drive (HDD) 104, a hard disk (HD) 105, a flexible disk drive (FDD) 106, a flexible disk (FD) 107 as an example of a removable recording medium, a display 108, an interface (I/F) 109, a keyboard 110, a mouse 111, a scanner 112, and a printer 113. Each constituent element is respectively connected by a bus 100.

The CPU 101 controls the entire genetic information display apparatus. The ROM 102 stores programs such as a boot program. The RAM 103 is used as a work area of the CPU 101. The HDD 104 controls read/write of data to and from the HD 105 as controlled by the CPU 101. The HD 105 stores data written under the control of the HDD 104.

The FDD 106 controls read/write of data to the FD 107 as controlled by the CPU 101. The FD 107 stores data written under the control of the FDD 106 or reads data stored on the FD 107 to a genetic information display apparatus.

A CD-ROM (CD-R, CD-RW), magneto-optical (MO), a digital versatile disk (DVD), or a memory card and the like can be also used as a removable recording medium apart from the FD 107. The display 108 displays a cursor, icons, or tool boxes, as well as data such as a text, images, and function information. A cathode ray tube (CRT), a thin film transistor (TFT) liquid crystal display, or a plasma display, for example, can be used for the display 108.

The I/F 109 is connected to a network 114 such as the Internet through a communication line, and is connected to other apparatuses via the network 114. The I/F 109 controls an internal interface with the network 114, and controls input and output of data from an external apparatus. A modem or a local area network (LAN) adapter, for example, can be used for the I/F 109.

The keyboard 110 includes keys for inputting characters, numbers, various instructions, and the like, and performs input of data. The keyboard 110 can be in the form of a touch panel-type input pad, a numerical keypad, and the like. The mouse 111 is used to move and select the range of the cursor or move and change the size of a window. It can also be a tracking ball or joystick or the like, provided it has the same function as a pointing device.

The scanner 112 optically reads images or scans image data within the genetic information display apparatus. The scanner 112 can also have an optical character reader (OCR) function. The printer 113 prints out image data and text data. A laser printer or ink jet printer can be used as the printer 113.

Figure 2:
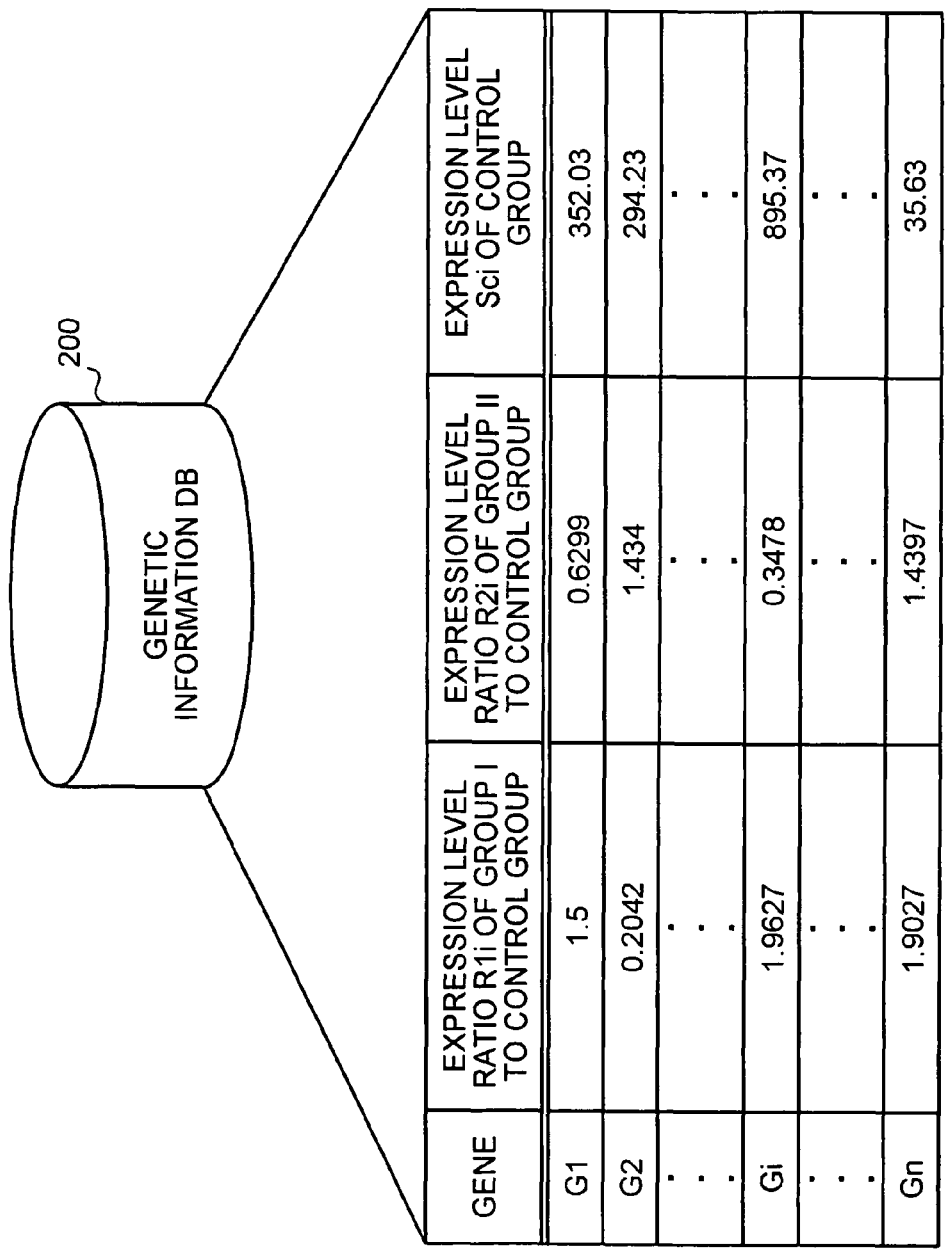
FIG. 2 is an explanatory diagram of a genetic information database (DB) according to the embodiment.

FIG. 2 is an explanatory diagram of a genetic information DB according to the embodiment. In FIG. 2, a genetic information DB 200 stores an expression level ratio $R1i$ ($0 \leq R1i$) of a group I relative to a control group, an expression level ratio $R2i$ ($0 \leq R2i$) of a group II relative to the control group, and an expression level Sci of the control group for each gene Gi (I=i to n), and more specifically, the function is realized by a recording medium such as the ROM 102, the RAM 103 or the HD 105, for example, shown in FIG. 1.

The control group refers to a common reference group for the subject sample groups I and II, and in this specification, its gene expression level is designated as a reference expression level Sci. The reference expression level Sci is the gene expression level in a predetermined state for a gene Gi in a certain tissue of an organism.

A group I is one of the subject sample groups for the control group, and in this specification, its gene expression level is designated as a first expression level $S1i$. The first expression level $S1i$ is the gene expression level in a specific state that differs from the predetermined state and under predetermined conditions for the gene Gi in a certain tissue of an organism.

A group II is the other subject sample group for the control group, and in this specification, its gene expression level is designated as a second expression level $S2i$. The second expression level $S2i$ is the gene expression level in a specific state that differs from the predetermined state and under predetermined conditions for the gene Gi in a certain tissue of an organism.

In an example in which the predetermined state is the normal state, the specific state is a disease state, the predetermined conditions refer to drug administration, other conditions refer to the absence of drug administration, and the organism is a mouse, the expression level Sci indicates, for example, the expression level of the gene Gi in normal tissue of the mouse. The first expression level $S1i$ indicates the expression level of the gene Gi in diseased tissue in the case of having administered a drug to the mouse. The second expression level $S2i$ indicates the expression level of the gene Gi in diseased tissue in the case of not having administered a drug to the mouse. The relationship among the control group, the group I and the group II is shown in Table 1 below.

TABLE 1

| | | Conditions | |
|---|---|---|---|
| | | Drug administration | Absence of drug administration |
| Tissue state | Normal | Reference expression level Sc (Control group) | |
| | Diseased | First expression level S1i (Group I) | Second expression level S2i (Group II) |

FIG. 3 is an explanatory diagram of gene coordinate data in a network diagram according to the embodiment. In FIG. 3, coordinates (X coordinate, Y coordinate) are set on the display screen for each gene Gi.

Figure 4:
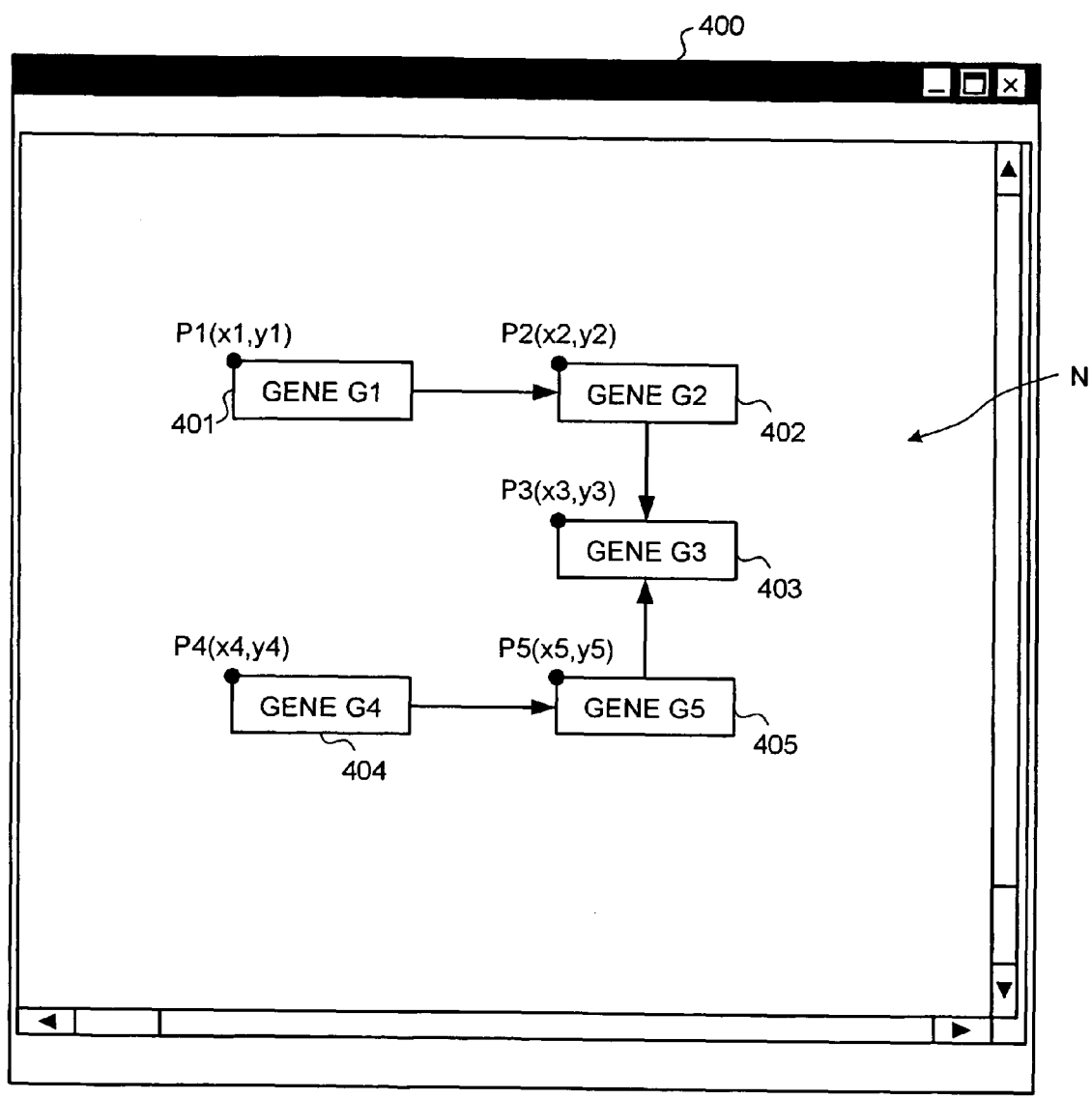
FIG. 4 is an explanatory diagram of a display example of the network diagram according to the embodiment.

FIG. 4 is an explanatory diagram of a display example of the network diagram according to the embodiment. In FIG. 4, a network diagram N relating to control of gene expression is displayed on a display screen 400 of the display 108 shown in FIG. 1.

The network diagram N is represented by image data 401 to 405 relating to each gene G1 to G5 and arrows between the image data 401 to 405, and is displayed using an image data format such as a bitmap, a JPEG, a GIF or a PDF. The network diagram N indicates the expression control of the genes G1 to G5, and the arrows between the image data 401 to 405 indicates the direction of the interactions relating to expression control. For example, the arrow between the image data 401 and 402 represents that the gene G1 controls (inhibits, for example) the expression of the gene G2.

In the network diagram N, the upper left corners P1 to P5 of the rectangular image data 401 to 405 indicating the genes G1 to G5 are points that specify the display locations of a pie chart to be described later, and correspond to the X and Y coordinates (x1, y1) to (x5, y5) of the gene Gi shown in FIG. 3. For example, since the coordinates of the gene G1 are (x1, y1) in FIG. 3, the pie chart of the gene G1 is displayed at a point P1 (x1, y1) of the image data 401. The network diagram N can use, for example, a pathway disclosed on the website of KEGG.

Figure 5:
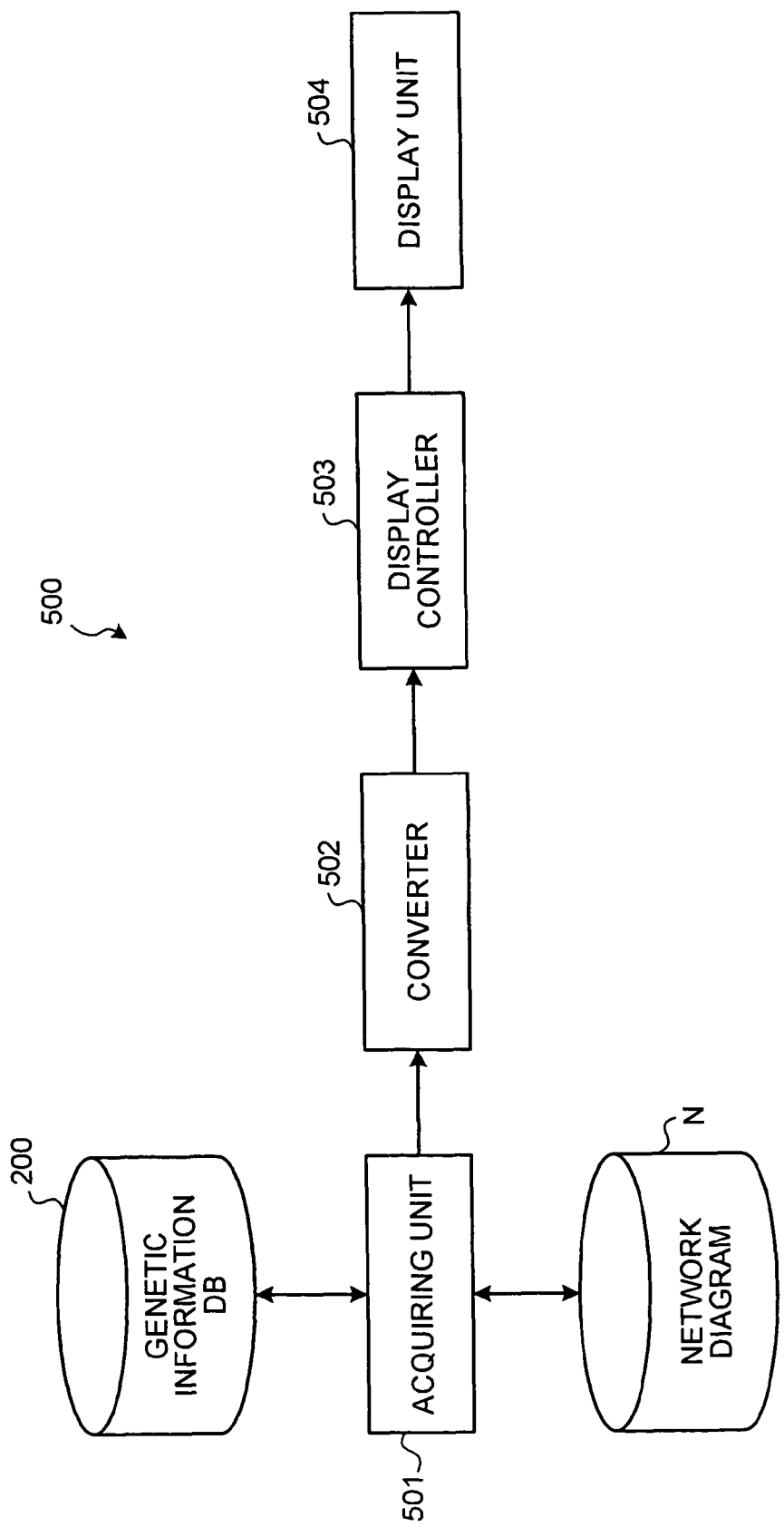
FIG. 5 is a block diagram of the functional configuration of the genetic information display apparatus according to the embodiment.

FIG. 5 is block diagram of the functional configuration of the genetic information display apparatus according to the embodiment. In FIG. 5, a genetic information display apparatus 500 is composed of the genetic information DB 200, the network diagram N, an acquiring unit 501, a converter 502, a display controller 503, and a display unit 504.

In FIG. 5, the acquiring unit 501 acquires an expression level ratio R1$i$, which is the ratio between the reference expression level Sci in a predetermined state of a tissue and the first expression level S1$i$ in a specific state that differs from the predetermined state of the tissue and under predetermined conditions, and an expression level ratio R2$i$, which is the ratio between the reference expression level Sci and a second expression level S2$i$ in a specific state of a tissue and under other conditions that differ from the predetermined conditions, for the gene Gi in the tissue of an organism.

With the example of a mouse for the organism, the acquiring unit 501 acquires the expression level ratio R1$i$ for the gene Gi in the tissue of an organism between the reference expression level Sci of normal tissue and the first expression level S1$i$ of diseased tissue in the case of having administered a drug. It also acquires an expression level ratio R2$i$ between the reference expression level Sci and the second expression level S2$i$ of diseased tissue in the case of not having administered a drug.

The acquiring unit 501 extracts the first expression level ratio R1$i$ and the second expression level ratio R2$i$ for the gene Gi from the genetic information DB 200 shown in FIG. 2. The acquiring unit 501 then acquires the first expression level S1$i$ in the form of a calculation result obtained by multiplying the reference expression level Sci and the first expression level ratio R1$i$. Similarly, the acquiring unit 501 acquires the second expression level S2$i$ in the form of a calculation result obtained by multiplying the reference expression level Sci and the second expression level ratio R2$i$. If the first expression level S1$i$ and the second expression level S2$i$ are preliminarily stored in the genetic information DB 200, they are acquired by extracting from the genetic information DB 200.

The converter 502 converts the scales of the expression level ratio R1$i$, the expression level ratio R2$i$, the first expression level S1$i$ and the second expression level S2$i$ acquired by the acquiring unit 501. With respect to the expression level ratios R1$i$ and R2$i$, for example, the converter 502 first designates the maximum value of all the expression level ratios R11 to R1$n$ and R21 to R2$n$ as Rmax, applies an arbitrary constant C (Rmax≦C), and calculates the expression level ratio T1$i$ and the expression level ratio T2$i$ following a scale conversion as shown the following equations (1) to (4). The expression level ratio T1$i$ following the scale conversion corresponds to a central angle $\theta 1i$ ($0 \leq \theta 1i \leq \pi$) of the pie chart for the group I, while the expression level ratio T1$i$ following the scale conversion represents a central angle $\theta 2i$ ($0 \leq \theta 2i \leq \pi$) in the pie chart for the group II.

When $0 \leq R1i \leq 1.0$, $T1i = -R1i$ (1)

When $1.0 < R1i$, $T1i = (R1i - 1.0)/(C - 1.0)$ (2)

When $0 < R2i \leq 1.0$, $T2i = -R2i$ (3)

When $1.0 < R2i$, $T2i = (R2i - 1.0)/(C - 1.0)$ (4)

The expression level ratios T1$i$ and T2$i$ following the scale conversion are displayed in a predetermined color (red, for example) if they are positive, and displayed in a color different from the predetermined color (green, for example) if they are negative.

Due to the large difference in expression levels with respect to the first expression level S1$i$ and the second expression level S2$i$, the converter 502 calculates a first expression level D1$i$ and a second expression D2$i$ following the scale conversion by carrying out a logarithmic scale conversion as shown in equations (5) and (6) below. The first expression level D1$i$ following the scale conversion becomes the radius of the pie chart of the group I (hereinafter, the radius is occasionally indicated as D1$i$), while the second expression level D2$i$ following the scale conversion becomes the radius of the pie chart of the group II (hereinafter, the radius is occasionally indicated as D2$i$).

K is a constant that indicates the unit of pixel increase/decrease. The conversion results of equations (1) to (6) are shown in FIG. 6. FIG. 6 is an explanatory diagram of conversion results obtained from the converter 502 according to the embodiment.

$D1i = K \cdot \log(S1i)$ (5)

$D2i = K \cdot \log(S2i)$ (6)

The display unit 504 has a display screen that displays a graph. The display unit 504 has a graphics memory, and the display screen is controlled by the display controller 503 (described later). This function is realized by the display 108 shown in FIG. 1.

The display controller 503 controls the display screen to display the expression level ratio R1$i$ (T1$i$) and the first expression level S1$i$ (D1$i$) under predetermined conditions acquired by the acquiring unit 501 with a first diagram that composes a graph, and displays the expression level ratio R2$i$ (T2$i$) and the second expression level S2$i$ (D2$i$) under other conditions acquired by the acquiring unit 501 with a second diagram that composes a graph.

Figure 7:
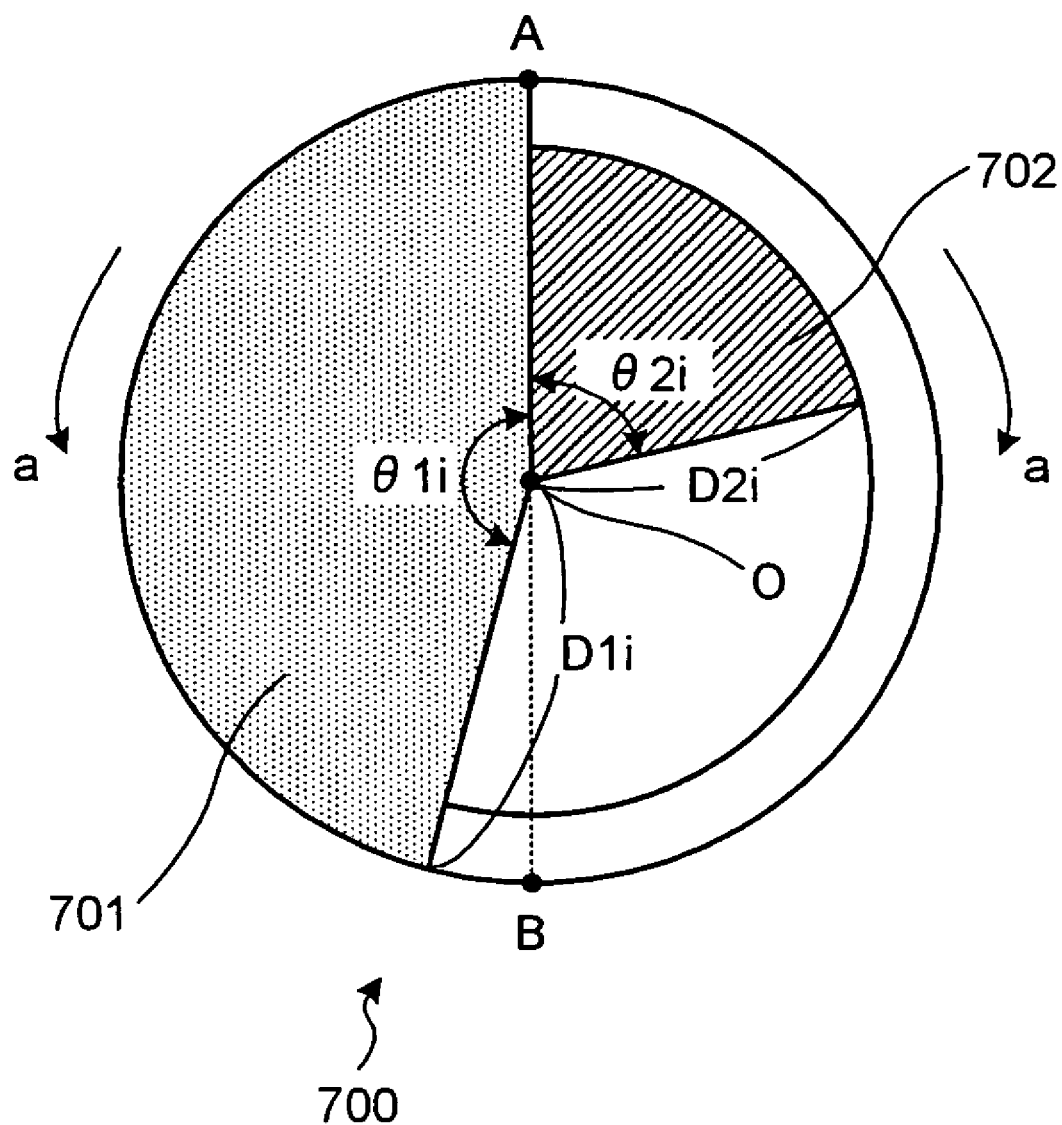
FIG. 7 is an explanatory diagram of an example of a pie chart according to the embodiment.

FIG. 7 is an explanatory diagram of an example of a pie chart according to the embodiment. In FIG. 7, a pie chart 700 is a pie graph that depicts genetic information of the gene Gi.

For example, the left half of the pie chart 700 is a display area that displays gene expression information of the group I, while the right half is a display area that displays gene expression information of the group II.

The gene expression information of the group I is displayed using the expression level ratio T1$i$ and the first expression level D1$i$. More specifically, the display controller 503 converts the expression level ratio T1$i$ to an angle θ1$i$ using the following equation (7), and displays it in the form of a pie sector 701 having the converted ƒ1$i$ as its central angle and the first expression level D1$i$ as its radius.

$$\theta 1i = \pi \cdot T1i \tag{7}$$

Similarly, the gene expression information of the group II is displayed using the expression level ratio T2$i$ and the second expression level D2$i$. More specifically, the display controller 503 converts the expression level ratio T2$i$ to an angle θ2$i$ using the following equation (8), and displays it in the form of the pie sector 701 having the converted θ2$i$ as its central angle and a first expression level D2$i$ as its radius.

$$\theta 2i = \pi \cdot T2i \tag{8}$$

Two points A and B lying on the circumference of the pie chart 700 are circumferential end points of the diameter that passes through a center O of the pie chart 700. The point A indicates that the central angles θ1$i$ and θ2$i$ are 0 rad, and the point B indicates that the central angles θ1$i$ and θ2$i$ are π rad. Thus, if the central angles θ1$i$ and θ2$i$ are both widened in the direction of arrows a in FIG. 7, since the central angles θ1$i$ and θ2$i$ become larger, the corresponding expression level ratios T1$i$ and T2$i$ are shown to increase.

The colors used in the pie sectors 701 and 702 represent the positive or negative nature of the expression level ratios T1$i$ and T2$i$. For example, if the expression level ratio is positive, the color inside the pie sector is depicted in a predetermined color (for example, red; indicated with dots in FIG. 7), and if the expression level ratio is negative, the color inside the pie sector is depicted with a color different from the predetermined color (for example, green; indicated with hatching in FIG. 7). Thus, the pie sector 701 shown in FIG. 7 represents the positive expression level ratio T1$i$, and the pie sector 702 shown in FIG. 7 represents the negative expression level ratio T2$i$.

The display controller 503 depicts the larger expression level among the first expression D1$i$ serving as the radius of the pie sector 701 that represents gene expression information of the group I and the second expression level D2$i$ serving as the radius of the pie sector 702 that represents the gene expression information of the group II, as the maximum radius of the pie chart 700. Namely, the size of the pie chart 700 is proportional to the magnitude of the expression level.

In this manner, the gene expression information of the group I and the group II can be compared intuitively as a result of displaying the pie sector 701 representing the gene expression information of the group I and the pie sector 702 representing the gene expression information of the group II laterally symmetrically in the pie chart 700. In particular, since the central angle θ1$i$ of the pie sector 701 of the group I and the central angle θ2$i$ of the pie sector 702 of the group II respectively correspond to the expression level ratio T1$i$ and the expression level T2$i$, and the radius of the pie sector 701 of the group I and the radius of the pie sector 702 of the group II respectively represent the first expression level D1$i$ and the second expression level D2$i$, multiple sets of the gene expression information (the expression level ratios and fluctuations in the expression levels of the groups I and II) can be understood simultaneously and intuitively.

The functions of the acquiring unit 501, the converter 502, and the display controller 503 are specifically realized by the CPU 101 running a program recorded on, for example, the ROM 102, the RAM 103 or the HD 105 shown in FIG. 1, or by the I/F 109.

Figure 8:
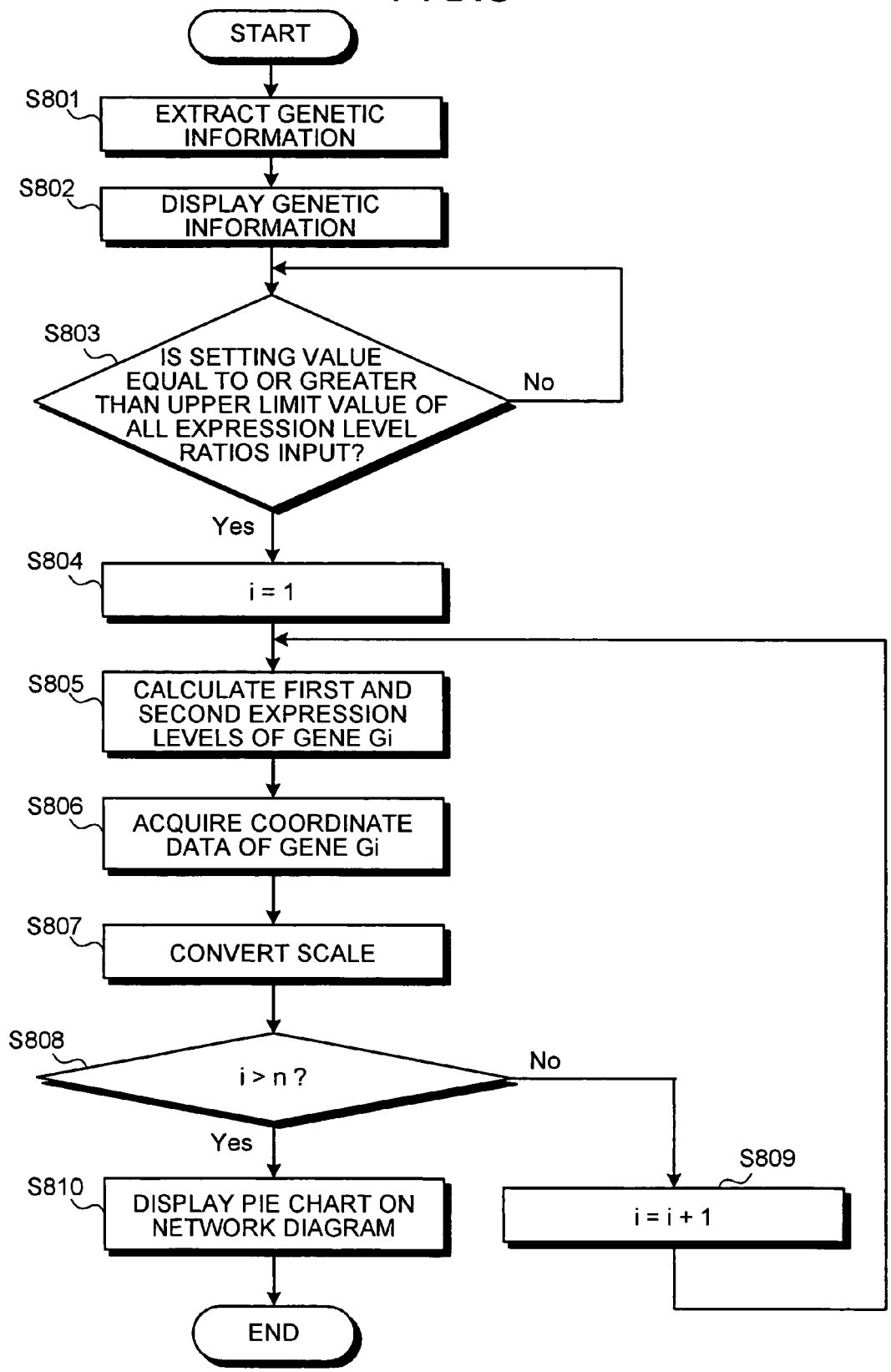
FIG. 8 is a flowchart of a process procedure of genetic information display according to the embodiment.

FIG. 8 is a flowchart of a process procedure of genetic information display according to the embodiment. In FIG. 8, the reference expression level Sc$i$, the first expression level ratio R1$i$ and the second expression level ratio R2$i$ for the gene G$i$ (G1-G$n$) to be displayed are first extracted as genetic information from the genetic information DB 200 (step S801). The extracted genetic information is then displayed on the display screen (step S802). Accordingly, a user can refer to the first expression level ratio R1$i$ and the second expression level R2$i$ displayed on the display screen.

After waiting for an operational input from the user (step S803: No), when a setting (constant C) has been input that is equal to or greater than the maximum expression level Rmax that is the upper limit value of all expression level ratios (step S803: Yes), i is set to 1 (step S804), and the first expression level S1$i$ and the second expression level S2$i$ of the gene G$i$ are calculated (step S805). The coordinate data (x$i$, y$i$) of the gene G$i$ is also acquired from the network diagram N (step S806).

A scale conversion process is then carried out by the converter 502 (step S807). Namely, an arithmetic process of the equations (1) to (6) is carried out to calculate T1$i$, T2$i$, D1$i$, and D2$i$.

If i>n is not established (step S808: No), then i is incremented by 1 (step S809) and the procedure returns to step S805. If i>n is established (step S808: Yes), then the pie chart 700 is displayed using the central angle θ1$i$, the radius D1$i$, the central angle θ2$i$, and the radius D2$i$ at the location specified with the coordinate data (x$i$, y$i$) on the network diagram N (step S810).

Figure 9:
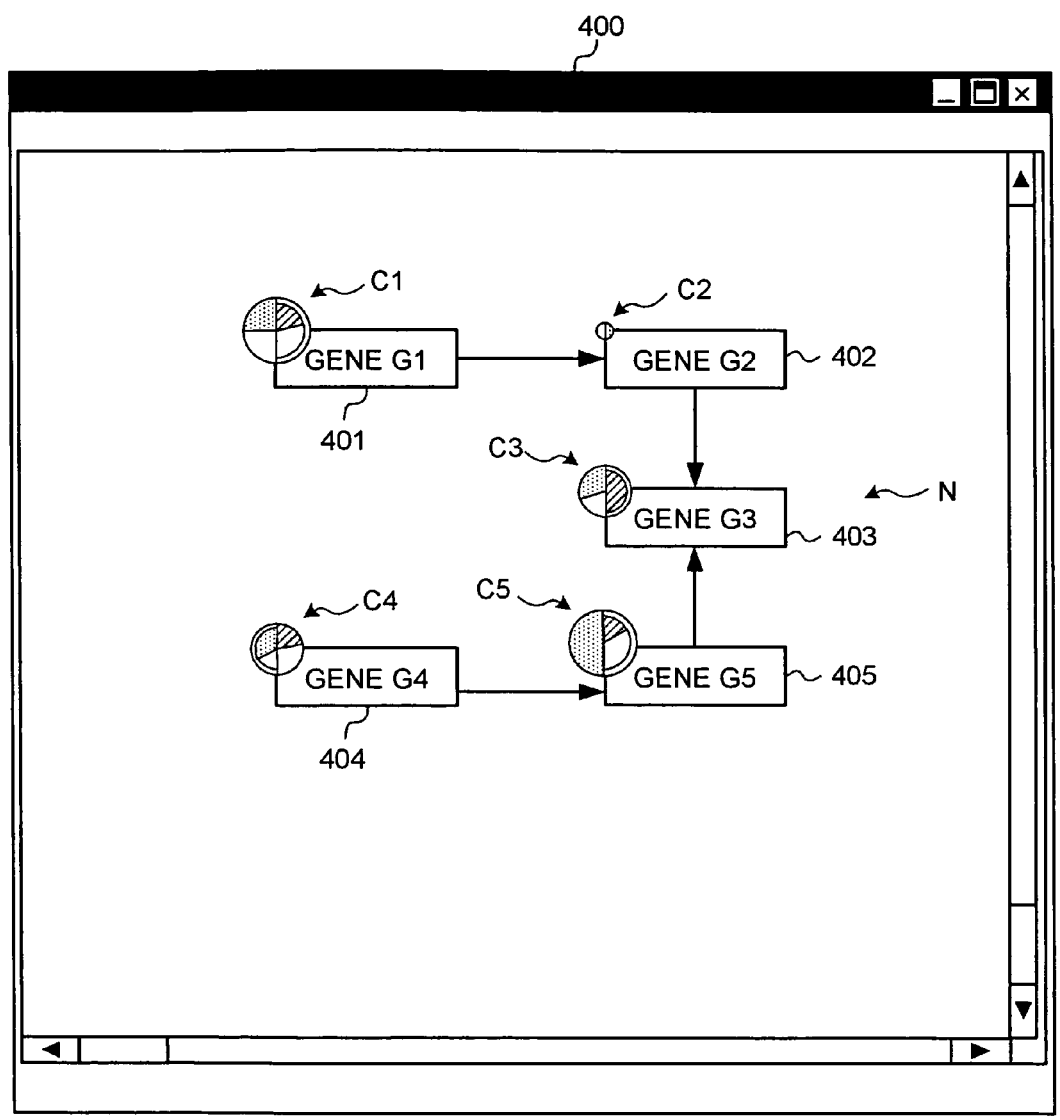
FIG. 9 is an explanatory diagram of a display example of the pie chart on the network diagram displayed by the genetic information display apparatus according to the embodiment.

FIG. 9 is an explanatory diagram of a display example of a pie chart on the network diagram N displayed by a genetic information display apparatus according to the embodiment. In FIG. 9, pie charts C1 to C5 are respectively displayed at the coordinate locations of each upper left corner of the image data 401 to 405 indicating the genes G1 to G5. These pie charts C1 to C5 can also be displayed semi-transparently.

Numerical values of the gene expression information (the first expression level S1$i$, the expression level ratio R1$i$, the second expression level S2$i$, and the expression level ratio R2$i$) prior to the scale conversion can also be displayed by pointing to the image data 401 to 405 with a pointing device. Accordingly, actual numerical values can be confirmed.

In this manner, because it is possible to display a pie chart that indicates the gene expression information for each gene G$i$ on the network diagram N, fluctuations (increase or decrease) in gene expression levels can be monitored. Moreover, because the expression level ratios are visually self-evident from the central angle of each pie sector, fluctuations in the expression level ratios can be recognized in an intuitive and readily understandable manner.

Furthermore, since tissue in a specific state (diseased tissue) under predetermined conditions (having been administered a drug) and tissue in a specific state (diseased tissue) under other conditions (having not been administered a drug) are visually self-evident from the radius of the pie sector, differences in gene expression levels (intensity) under different conditions and fluctuations in the expression level ratios can be recognized in an intuitive and readily understandable manner.

Although the pie chart 700 is depicted in this embodiment by using the angle θ1$i$ corresponding to the expression level ratio T1$i$ and the angle θ2$i$ corresponding to the expression level ratio T2$i$ as the central angles of the pie sectors 701 and 702, and using the first expression level D1$i$ and the second expression level D2$i$ as radii of the pie sectors 701 and 702, the first expression level D1$i$ and the second expression level D2$i$ can also be represented by the central angle θ1$i$ and the central angle θ2$i$ in the pie sectors 701 and 702 by converting to the angles as in the equations (7) and (8), by using the expression level ratio T1$i$ and the expression level ratio T2$i$ as radii of the pie sectors 701 and 702.

As has been explained above, genetic information can be understood intuitively and clearly by making gene expression information more legible.

The genetic information display method described in the embodiment can be realized by making a computer, such as a personal computer or a work station, execute a program that is prepared beforehand. The program is stored in a computer-readable recording medium, such as an HD, an FD, a CD-ROM, a MO, a DVD, and the like, and is executed by being read from the recording medium by the computer. The program may be a transmission medium that can be distributed via a network such as the Internet.

According to the present invention, gene expression information can be understood intuitively and clearly.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. An apparatus for displaying genetic information, the apparatus being configured to allow a graphical representation of genes that enables a comparison between genes based on their interaction, comprising:
    an acquiring unit configured to acquire, for a gene in a tissue of an organism,
        a predetermined-conditions-expression level ratio that is a ratio between a reference expression level in a predetermined state of the tissue and a first expression level under first conditions in a specific state that differs from the predetermined state of the tissue, and
        an other-conditions-expression level ratio that is a ratio between the reference expression level and a second expression level under second conditions in the specific state of the tissue; and
    a displaying unit with a display screen; and
    a display controller configured to control the displaying unit to display on the display screen
        the predetermined-conditions-expression level ratio and the first expression level with a first diagram that is part of a graph, and
        the other-conditions-expression level ratio and the second expression level with a second diagram that is part of the graph,
    wherein
        the graph is a pie chart, and the first diagram and the second diagram are a first pie and a second sector, respectively, in the pie chart, wherein
        the first diagram is a diagram in which the predetermined-conditions-expression level ratio is represented as a first central angle of the first pie sector, and the first expression level is represented as a first radius of the first pie sector, and
        the second diagram is a diagram in which the other-conditions-expression level ratio is represented as a second central angle of the second pie sector, and the second expression level is represented as a second radius of the second pie sector, and
    the acquiring unit acquires coordinate data that indicate a location of the gene on a network diagram relating to gene expression control, and
    the display controller controls the displaying unit so as to display the network diagram on the display screen, wherein the network diagram is represented by image data relating to each gene and an arrow in the image data indicates a direction of interactions relating to expression control, a gene from which the arrow originates controlling an expression in a different gene at a tip of the arrow, and displays the graph at the location on the network diagram specified by the coordinate data.

2. The apparatus according to claim 1, wherein
    the first diagram is a diagram in which an absolute value of the predetermined-conditions-expression level ratio is represented as the first central angle of the first pie sector, and the first pie sector is displayed in a first color when the predetermined-conditions-expression level ratio is positive, and the first pie sector is displayed in a second color different from the first color when the predetermined-conditions-expression level ratio is negative, and
    the second diagram is a diagram in which an absolute value of other-conditions-expression level ratio is represented as the second central angle of the second pie sector, and the second pie sector is displayed in a third color when the other-conditions-expression level ratio is positive, and the second pie sector is displayed in a fourth color different from the third color when the other-conditions-expression level ratio is negative.

3. An apparatus for displaying genetic information, the apparatus being configured to allow a graphical representation of genes that enables a comparison between genes based on their interaction, comprising:
    an acquiring unit configured to acquire, for a gene in a tissue of an organism,
        a predetermined-conditions-expression level ratio that is a ratio between a reference expression level in a predetermined state of the tissue and a first expression level under first conditions in a specific state that differs from the predetermined state of the tissue, and
        an other-conditions-expression level ratio that is a ratio between the reference expression level and a second expression level under second conditions in the specific state of the tissue; and
    a displaying unit with a display screen; and
    a display controller configured to control the displaying unit to display on the display screen
        the predetermined-conditions-expression level ratio and the first expression level with a first diagram that is part of a graph, and
        the other-conditions-expression level ratio and the second expression level with a second diagram that is part of the graph,
    wherein
        the graph is a pie chart, and the first diagram and the second diagram are a first pie and a second sectors, respectively, in the pie chart, and
    the acquiring unit acquires coordinate data that indicate a location of the gene on a network diagram relating to gene expression control, and
    the display controller controls the displaying unit so as to display the network diagram on the display screen, wherein the network diagram is represented by image data relating to each gene and an arrow in the image data indicates a direction of interactions relating to expression control, a first gene from which the arrow originates controlling an expression in a different gene at a tip of the arrow, and displays the graph at the location on the network diagram specified by the coordinate data, wherein the first diagram represents the first expression level as a first central angle of the first pie sector, and represents the predetermined-conditions-expression level ratio as a first radius of the first pie sector, and the second diagram represents the second expression level as a second central angle of a second pie sector, and represents the other-conditions-expression level ratio as a second radius of the pie sector.

4. The apparatus according to claim 1, wherein the reference expression level is a gene expression level of normal tissue in the organism, the first expression level is a gene expression level in the case of having administered a drug to diseased tissue of the organism, and the second expression level is a gene expression level in the case of not having administered the drug to the diseased tissue of the organism.

5. A method for displaying genetic information, the method allowing a graphical representation of genes that enables a comparison between genes based on their interaction comprising:

acquiring, for a gene in a tissue of an organism,
a predetermined-conditions-expression level ratio that is a ratio between a reference expression level in a predetermined state of the tissue and a first expression level under first conditions in a specific state that differs from the predetermined state of the tissue, and
an other-conditions-expression level ratio that is a ratio between the reference expression level and a second expression level under second conditions in the specific state of the tissue;

displaying on a display screen the predetermined-conditions-expression level ratio and the first expression level with a first diagram that is part of a graph, and the other-conditions-expression level ratio and the second expression level with a second diagram that is part of the graph, wherein the graph is a pie chart, and the first diagram and the second diagram are a first and a second pie sector in the pie chart, wherein the first diagram is a diagram in which the predetermined-conditions-expression level ratio and the first expression level are represented as one of a first central angle and a first radius of the first pie sector, respectively, and the second diagram is a diagram in which the other-conditions-expression level ratio and the second expression level are represented as one of a second central angle and a second radius of the second pie sector, respectively;

acquiring coordinate data that indicate a location of the gene on a network diagram relating to gene expression control;

controlling the displaying to display the network diagram on the display screen by a central processing unit, wherein the network diagram is represented by image data relating to each gene and an arrow in the image data indicates a direction of interactions relating to expression control, a gene from which the arrow originates controlling an expression in a different gene at a tip of the arrow; and displaying the network diagram on the display screen, and displaying the graph at the location on the network diagram specified by the coordinate data.

6. A computer-readable recording storage medium configured to store therein a computer program that causes a computer to implement a method for displaying genetic information, allowing a graphical representation of genes that enables a comparison between genes based on their interaction, the computer program causing the computer to execute:

acquiring, for a gene in a tissue of an organism,
a predetermined-conditions-expression level ratio that is a ratio between a reference expression level in a predetermined state of the tissue and a first expression level under first conditions in a specific state that differs from the predetermined state of the tissue, and
an other-conditions-expression level ratio that is a ratio between the reference expression level and a second expression level under second conditions in the specific state of the tissue;

displaying on a display screen the predetermined-conditions-expression level ratio and the first expression level with a first diagram that is part of a graph, and the other-conditions-expression level ratio and the second expression level with a second diagram that is part of the graph, wherein the graph is a pie chart, and the first diagram and the second diagram are a first and a second pie sector in the pie chart, wherein the first diagram is a diagram in which the predetermined-conditions-expression level ratio and the first expression level are represented as one of a first central angle and a first radius of the first pie sector, respectively, and the second diagram is a diagram in which the other-conditions-expression level ratio and the second expression level are represented as one of a second central angle and a second radius of the second pie sector, respectively;

acquiring coordinate data that indicate a location of the gene on a network diagram relating to gene expression control;

controlling the displaying to display the network diagram on the display screen, wherein the network diagram is represented by image data relating to each gene and an arrow in the image data indicates a direction of interactions relating to expression control, a gene from which the arrow originates controlling an expression in a different gene at a tip of the arrow; and displaying the network diagram on the display screen, and displaying the graph at the location on the network diagram specified by the coordinate data.

7. The apparatus according to claim 3, wherein the reference expression level is a first gene expression level of the normal tissue in the organism, the first expression level is a gene expression level after a drug has been administered to a diseased tissue of the organism, and the second expression level is a second gene expression level wherein the drug has not been administered to the diseased tissue of the organism.

* * * * *